United States Patent [19]

Curtis

[11] Patent Number: 4,461,288
[45] Date of Patent: Jul. 24, 1984

[54] MID-HIND FOOT STABILIZER

[76] Inventor: R. Stephen Curtis, 2828 Lemmon Ave., Dallas, Tex. 75204

[21] Appl. No.: 524,428

[22] Filed: Aug. 18, 1983

[51] Int. Cl.³ .............................................. A61F 5/04
[52] U.S. Cl. .................................. 128/80 H; 128/166
[58] Field of Search ............. 128/166, 80 H; 36/58.5, 36/119

[56] References Cited

U.S. PATENT DOCUMENTS

| | | |
|---|---|---|
| 430,982 | 6/1890 | Ziegler . |
| 950,862 | 3/1910 | Nelson . |
| 1,089,073 | 3/1914 | Palmer . |
| 1,110,362 | 9/1914 | Whitaker . |
| 1,252,149 | 1/1918 | Muse . |
| 1,546,551 | 7/1925 | Petri ................................. 128/80 H |
| 1,655,715 | 1/1928 | Sneeston . |
| 2,233,544 | 3/1941 | McKinley . |
| 2,592,739 | 4/1952 | Richardson ..................... 128/166 X |
| 2,741,039 | 4/1956 | Mathews . |
| 3,047,967 | 8/1962 | Hoyt et al. . |
| 3,618,598 | 11/1971 | Davis ............................. 128/166 X |
| 3,777,751 | 12/1973 | Wise .................................... 128/166 |

FOREIGN PATENT DOCUMENTS 31283 1/1908 Fed. Rep. of Germany ...... 128/166

Primary Examiner—John D. Yasko
Attorney, Agent, or Firm—Jerry W. Mills; Gregory M. Howison; Jerry R. Selinger

[57] ABSTRACT

A stabilizing strap (25) for exterior use with a shoe (28) including a dorsal strap (26), an Achilles strap (30) and a plantar strap (32). One end of the dorsal strap (26), the Achilles strap (30) and the plantar strap (32) are connected together at a point (34) on the medial side of the foot. The other end of the plantar strap (32) is attached to two connecting straps (36) and (38). Two ring clasps (42) and (44) are attached to the end of the connecting straps (36) and (38) for receiving the free ends of the dorsal strap (26) and the Achilles strap (30). A fibrous layer (52) and a hook-like layer (50) are disposed on the exterior of the Achilles strap (30) such that the free end thereof can be pulled through the ring clasp and attached thereto. A fibrous layer (48) and a hook-like layer (46) are disposed on the exterior of the dorsal strap (26) to provide a similar attachment. By tensioning the dorsal strap (26) and the Achilles strap (30), a stabilizing force can be directed along the line of motion of the infratalar joints of the foot to prevent excess pronation thereof during exercise.

18 Claims, 8 Drawing Figures

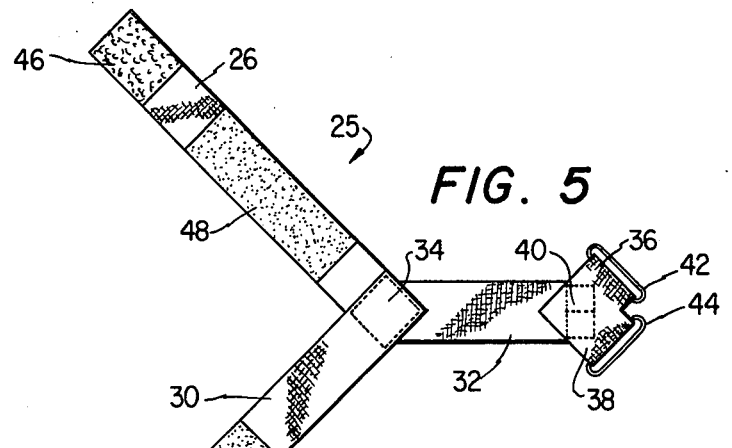
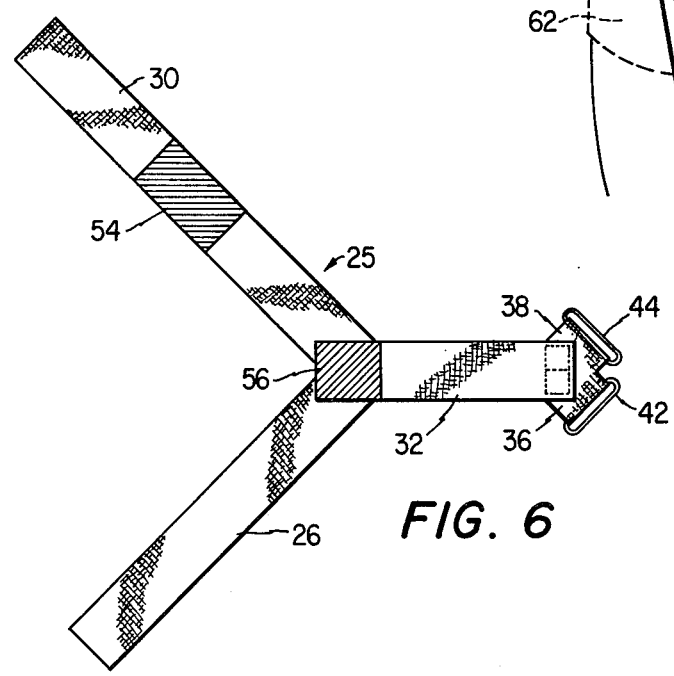

MID-HIND FOOT STABILIZER

TECHNICAL FIELD

The present invention pertains to an apparatus for stabilizing the foot joints during exercise and, more particularly, to a stabilizer strap worn external to a shoe for stabilizing the subtalar joint during the exercise.

BACKGROUND OF THE INVENTION

During exercise, the joints of an athlete's foot are subjected to most severe shear forces. In particular, the joint between the talus bone and the calcaneus bone, which forms the subtalar joint, is the recipient of a large portion of these shear forces. Primarily, these forces are the result of shocks generated when the heel strikes the ground. These shocks are exacerbated during running, since, during the running gait, both feet simultaneously leave the ground. As the heel strikes the ground during running, an increased motion occurs in all of the foot joints, with the forces distributed thereover by hydraulic action. This hydraulic action is due to the talar bones being held together by an integral network of muscles, tendons and ligaments that allow only limited motion, thus resulting in dispersion of the forces throughout the foot.

Although there is only limited motion between the talar bones, a certain amount of movement is provided in order to stabilize the foot on uneven surfaces. Such movements are inversion (pronation) which is turning of the foot inward and eversion (supination) which is turning the foot outward. When the heel of the foot strikes the ground, the remainder of the foot lags such that all of the weight is supported by the calcaneus bone. Until the distal portion of the foot strikes the ground, the foot is allowed to rotate about the subtalar joint which can cause excessive pronation. Normally, an adequate pair of athletic shoes can reduce this excessive pronation by providing arch support. However, athletic shoes have a tendency to slip during exercise and do not properly stabilize the subtalar joint. Moreover, an athlete's foot often swells during exercise, thus changing the fit and support of the athletic shoe during the exercise. If the subtalar joint and the joints therearound are not continually properly stabilized, pain can result from excessive rotation about these joints.

In view of the above, there exists a need for a stabilizing device that minimizes movement of the subtalar joint of the foot during exercise, and which may be adjusted during exercise in order to maintain proper support at all times.

SUMMARY OF THE INVENTION

The present invention disclosed and claimed herein comprises an apparatus for stabilizing movement of the infratalar joints of the foot and includes a dorsal strap for applying a dispersive force about the dorsum of the foot and directed along the line of motion of the infratalar joint. An Achilles strap is provided for applying a dispersive force about the tendo-calcaneus proximate the attachment point thereof to the calcaneus bone and directed towards the posterior talo-calcaneal joint. A plantar strap is provided for applying a dispersive force about the sole of the foot proximate the attachment point of the plantar fascia to the calcaneus bone and directed towards the infratalar joints. The dorsal strap, Achilles strap and plantar strap reduce movement of the infratalar joints during exercise and are interconnected such that an increase of force on one of the straps distributes the force to the remaining straps.

In another embodiment of the present invention, the straps are interconnected on the medial side of the foot adjacent the tendon connections to the navicular bone and adjustably connected together on the lateral side of the foot. The lateral connection allows for adjustment of the length of the Achilles and dorsal straps such that the force can be distributed around the infratalar joints. By adjusting these straps, compensation can be made for swelling in the foot and also different magnitudes of force therefor.

In yet another embodiment of the present invention, a shoe is first disposed over the foot and the straps placed external to the shoe to secure the shoe to the foot in addition to stabilizing the infratalar joints. In this manner, the straps assist the function of the shoe in distributing the forces incurred during running. The strap can be external to the shoe or an integral part thereof.

BRIEF DESCRIPTION OF THE DRAWINGS

For a more complete understanding of the present invention and the advantages thereof, reference is now made to the following description taken in conjunction with the accompanying Drawings in which:

FIG. 5 illustrates a planar view of the inner side of the apparatus unwrapped from the shoe;

FIG. 6 illustrates a planar view of the other side of the strap of FIG. 4;

FIG. 8 illustrates a top view of the instep pad disposed over the dorsum of the foot and integral with the shoe.

DETAILED DESCRIPTION OF THE INVENTION

Figure 1:
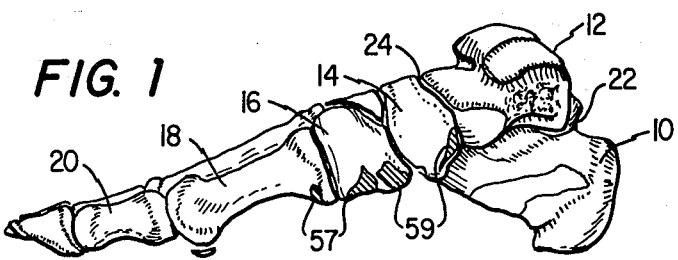
FIG. 1 illustrates a side view of the tarsal bones and depicting the infratalar joint.

In order to fully understand the present invention, an explanation of the construction of the human foot is necessary. Referring to FIG. 1, there is illustrated a medial view of the tarsal bones of the human foot. The heel of the foot is formed with the calcaneus bone 10 which is the largest and strongest of the tarsal bones. The calcaneus 10 articulates with the talus 12 and the navicular 14. The remainder of the foot is formed by articulation between the cuneiform bones 16, which articulate with the navicular 14, the metatarsals 18 which articulate at the base thereof with the cuneiform bones 16 and at the distal end with the phalanges 20. The superior surface of the talus 12 has a broad smooth trochlear surface for articulation with the tibia. The internal surface of the talus 12 presents at its upper part a pear-shaped articular facet for articulation with the inner malleolus and the external surface presents a large triangular facet, concave from above downward for articulation with the external malleolus.

The head of the talus 12 articulates with the navicular and the inferior surface thereof presents two articular facets separated by a deep groove. This groove runs obliquely forward and outward, becoming gradually broader and deeper in front, and corresponds with a similar groove on the upper surface of the calcaneus 10 and forms, while articulated with the calcaneus 10, a canal, filled up by the interosseous talo-calcanean ligament. There are three facets for articulation between the talus 12 and the calcaneus 10, the posterior, middle and anterior facets. Of these articular facets, the posterior is the larger, of an oblong form and deeply concave from side to side. The anterior and middle facets are shorter and narrower of an elongated oval form, convexed longitudinally.

The talus 12 takes part in three joints, the supratalar joint (not shown), the infratalar joints 22 and the pretalar joint 24. The supratalar joint is the ankle joint which is the articulation of the talus 12 with the tibia and allows flexion and extension of the foot. The operation of the supratalar joint is essentially that of a huge joint. The infratalar joints 22 permit a gliding of one bone on the other in a direction from side to side. The pretalar joint 24 permits considerable mobility and essentially consists of a rotation motion. Therefore, the infratalar joints 22 and the pretalar joints 24 provide means by which the sole of the foot may be slightly flexed and extended or carried inward (inversion or supination) and outward (eversion or pronation). During exercise, the infratalar joints 22 and the pretalar joints 24 are subject to an undue amount of stress when the heel of the foot strikes the ground. Although there are numerous ligaments that bind the tarsal bones together, excessive supination or pronation can result. This excessive supination or pronation can cause pain or discomfort to the individual due to excessive movement in the infratalar and pretalar joints.

Figure 2:
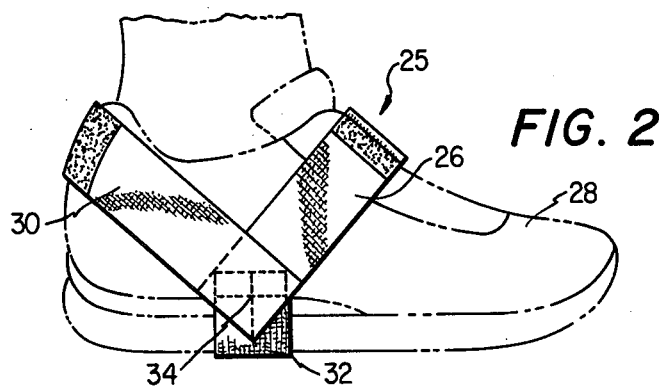
FIG. 2 illustrates a lateral view of the apparatus of the present invention disposed external to a shoe.
Figure 3:
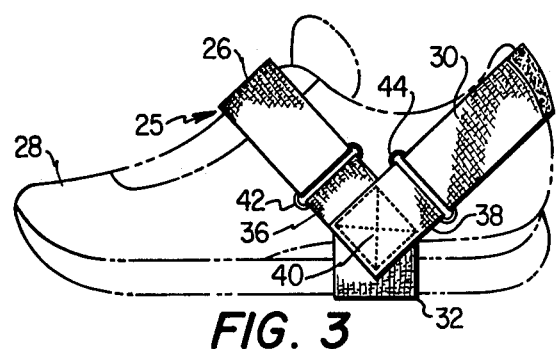
FIG. 3 illustrates a medial view of the apparatus of the present invention disposed external to the shoe.
Figure 4:
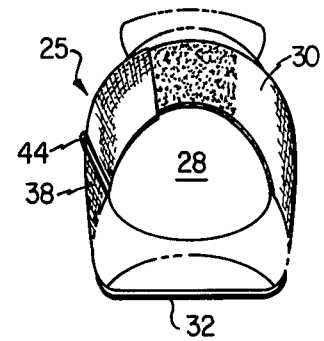
FIG. 4 illustrates a rear view of the shoes of FIGS. 1 and 2 with the apparatus disposed thereon.

Referring now to FIGS. 2, 3 and 4, there are illustrated medial, lateral and rear views of a stabilizing strap 25 in accordance with the present invention disposed external to a shoe 28. A dorsal strap 26 is disposed exterior to the shoe 28 on the dorsum of the foot. An Achilles strap 30 is disposed over the tendo-calcaneus adjacent the attachment point thereof to the calcaneus bone. A plantar strap 32 is disposed under the sole of the shoe 28 proximate the attachment point of the plantar fascia to the calcaneus bone 10. One end of each of the straps 26, 30 and 32 is secured together on the medial side of the shoe 28 at a connecting point 34. The straps 26, 30 and 32 are fabricated from a cotton polyester blend webbing. In the preferred embodiment, the plantar strap 32 has a thickness that is approximately twice the thickness of the Achilles strap 30 and the dorsal strap 26 since, as will be described hereinbelow, a greater magnitude of force is imparted to the plantar strap 32.

The other end of the plantar strap 32 has a length of connecting strap 36 and a length of connecting strap 38 attached thereto to a connecting point 40, the connecting straps 36 and 38 having a fixed oblique angle with respect to the center line of the plantar strap 32. The angles between each of the connecting straps 36 and 38 and the center line of the plantar strap 32 are similar to the angles between both the Achilles strap 30 and the dorsal strap 26 and the center line of the other end of the plantar strap 32. The connecting point 34 and the connecting point 40 are sewn on the ends of the plantar strap 32 to maintain all angular relationships.

A ring clasp 42 is connected to the free end of the connecting strap 36 and a ring clasp 44 is connected to the free end of the connecting strap 38. The ring clasp 42 is operable to receive the free end of the dorsal strap 26 and the ring clasp 44 is operable to receive the free end of the Achilles strap 30. The free ends of the straps 26 and 30 are turned back over and connected to the surfaces thereof after tensioning thereof, as will be described hereinbelow.

Referring now to FIGS. 5 and 6, there are illustrated two views of both sides of the stabilizing strap 25 removed from the shoe 28 and depicted as a planar view. In FIG. 4, the view illustrated is that of the surface of the stabilizing strap 25 facing away from the surface of the shoe 28. A layer 46 of hook-like material is disposed proximate the end of the dorsal strap 26. A layer 48 of fibrous material is disposed on the surface of the dorsal strap 26 adjacent the layer 46. The hook-like material in the layer 46 is operable to mesh with the fibrous material in the layer 48 to form an attachment therefor. This type of material is commonly referred to under the trade name "Velcro". A layer of hook-like material 50 is disposed proximate the end of the strap 30 and a layer of fibrous material 52 is disposed adjacent the layer of hook-like material 50. The layers 50 and 52 are similar to the layers 46 and 48, respectively.

The free end of the dorsal strap 26 having the layer 46 disposed thereon is inserted through the ring clasp 42 on the connecting strap 36 and folded back over itself such that the layer 46 contacts the layer 48 on the surface thereof. The two layers 46 and 48 are designed to provide a resistance to shear forces therebetween but the application of forces perpendicular to the surface of the dorsal layer 26 at the connection between the layers 46 and 48 results in separation thereof. Therefore, the dorsal strap 26 can be tightened through the ring clasp 42 and the two layers 46 and 48 attached together to provide sufficient shear force to retain the tension therein. The free end of the strap 30 is inserted through the ring clasp 44 in a similar manner with the layers 50 and 52 providing the attachment therefor.

Referring now to FIG. 6, a force relief pad 54 is attached to the surface of the Achilles strap 30 such that the pad 54 is adjacent the surface of the shoe 28. The pad 54 is oriented on the surface of the strap 30 such that the pad will cover the tendo-calcaneus and evenly disperse the force across the surface and the sides thereof. A force relief pad 56 is disposed on the opposite side of the connection point 34 for contacting the medial side of the shoe 28. The pads 54 and 56 are fabricated of neoprene rubber in the preferred embodiment.

As described above, the connection point 34 is disposed adjacent and slightly below the navicular bone. This portion of the foot anatomy is very sensitive in that both the anterior tibial tendon and posterior tibial tendons attach in this region. Referring back to FIG. 1, the anterior tibial tendon attaches to the points 57 on the cuneiform bone 16 and the base of the first metatarsal bone. The posterior tibial tendon attaches to the points 59 on the undersurface of the navicular bone 14 and the cuneiform bone 16. The posterior and anterior tibial tendons extend about the navicular tuberosity and can be a point of irritation during exercise. Therefore, the force relief pad 56 provides some conformation to the lateral side of the foot and, in addition, raises the dorsal strap 26 at the connection point 34 slightly above the surface of the shoe 28. In this manner, the pressure applied to the area proximate the navicular tuberosity and the insertion points of the anterior and posterior tibial tendons is minimized.

Referring further to FIGS. 5 and 6, the operation of the dorsal, Achilles and plantar straps will be described in more detail. Prior to exercise, the plantar strap 32 is disposed under the sole of the shoe, the Achilles strap 30 placed over the back of the shoe and the dorsal strap 26 placed over the dorsum of the shoe. The free ends of the dorsal strap 26 and the Achilles strap 30 are inserted through the ring clasps 42 and 44, respectively. The individual then tightens the dorsal strap 26 and the Achilles strap 30 to provide a desired level of comfort and support. The plantar strap 32 supplies a force vector that is directed towards the infratalar joints and proximate the attachment point of the planta fascia to the calcaneus bone. The Achilles strap 30 provides a force vector directed external to the shoe 28 and along the line of motion of the infratalar joints external to the tendo-calcaneus and proximate the attachment point thereof to the calcaneus bone. This force vector is transmitted to the infratalar joints by hydraulic action in the foot.

The dorsal strap 26 provides a force vector that is directed external to the shoe 28 and on the dorsum of the foot and essentially along the line of motion of the infratalar joints. When a shock is received to the foot during exercise, force applied to one portion of the foot, such as the heel, is dispersed through the foot by hydraulic action. The dorsal strap 26, Achilles strap 30 and plantar strap 32 aid the foot in dispersing this motion without excess movement of the infratalar joints and also improves shoe-foot conformation.

The shoe-foot conformation provided by the present invention is important in that the arch of the foot contacts the inner sole of the shoe 28 which is normally formed as an arch support to provide support for the arch of the foot. If the foot is allowed to slip within the shoe 28, support for the arch would be reduced and this would result in excess pronation of the foot since the lateral side of the foot would exhibit a tendency to turn outward during impact of the heel which can result in some pain. Therefore, the increased shoe-foot conformation provided by the stabilizing strap 25 can alleviate some of the pain due to excess pronation of the foot resulting from movement of the infratalar joints.

Since the tension of each of the straps 26 and 30 can be adjusted by the individual, the amount of force applied along the line of motion of the infratalar joints can therefore be adjusted. For example, during running, the foot can have a tendency to swell and sweat resulting in a change in the shoe-foot conformation. In order to adjust this, it is only necessary to adjust the tension in each of the straps. Sometimes this may require two or three adjustments during an exercise routine. Without allowing for adjustment of the straps 26 and 30, a great deal of discomfort could result during the exercise routine.

In the preferred embodiment, the angle between the center lines of the straps 26 and 30 is approximately 90° and the angle of each of the straps 26 and 30 with respect to the center line of the plantar strap 32 is approximately 45° such that the straps 26, 30 and 32 form a "Y" configuration. In a similar manner, the angle between the connecting straps 36 and 38 is approximately 90° and the angle of each of the straps 36 and 38 with respect to the center line of the plantar strap 32 is approximately 45°. However, it should be understood that the angular relationships of the straps in the preferred embodiment is not a limitation and can be altered to provide a stabilizing strap customized for an individual's personal foot anatomy. In addition, the attachment points 34 and 40, although shown fixed, can be pivoted such that the dorsal strap 26 and the Achilles strap 30 pivot about the attachment point 34 and the connecting straps 36 and 38 pivot about the connecting point 40. This allows an individual to place the straps 26 and 30 at the position to provide maximum stabilization of the infratalar joints. In addition to providing force relief, the pad 54 also provides friction to keep the strap 30 from moving. Although not shown, an additional pad can be disposed on the undersurface of the dorsal strap 26 to prevent slipping thereof. This maintains the selected position of the straps 26 and 30 with respect to the shoe.

Figure 7:
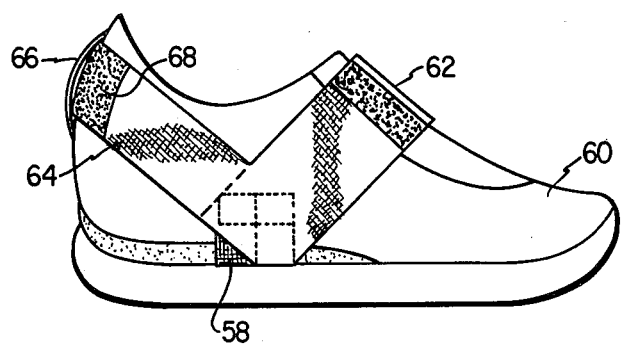
FIG. 7 illustrates a side view of an alternate embodiment of the apparatus of the present invention shown as an integral part of the shoe.

Referring now to FIG. 7, there is illustrated an alternate embodiment of the present invention. Points 58 are integrally molded with the sole of a shoe 60. A dorsal strap 62 is disposed over the dorsal of the foot external to the shoe 60 in a similar manner to the dorsal strap 26. However, the dorsal strap 62 is wider than the dorsal strap 26 of FIG. 2 with relation to the respective one of the shoes 28 or 60. An Achilles strap 64 is disposed over the tendo-calcaneus in a similar manner to the positioning of the Achilles strap 30. However, the Achilles strap 64 is permanently rooted through a slip 66 in the heel of the shoe and disposed higher than the dorsal strap 62. A pad 68 is disposed on the undersurface of the Achilles strap 64 and provides relief for the medial portion of the tendo-calcaneus. Although not shown, the Achilles strap 64 and the dorsal strap 62 have a free end which is inserted through associated ring clasps on the medial side of the shoe 60 that are similar to the ring clasps 42 and 44 of the embodiment of FIGS. 2-4. In addition, a relief pad (not shown) is disposed under the connection point for the straps 62 and 64 on the medial side of the strap 58.

Referring to FIG. 8, there is illustrated a top view of the shoe 60 of FIG. 7. A pad 70 is provided on the instep under two instep flaps 72 and 74. The dorsal strap 62 is illustrated in phantom lines. The pad 70 is similar in construction to the pads 54 and 56 of FIG. 6 and provides force relief over the dorsum of the foot and proximate to the sensitive tendon insertion points thereon. When the dorsal strap 62 is tightened, the flaps 72 and 74 move together to tighten the shoe 60 about the instep of the foot. Therefore, the Achilles strap 64 and the dorsal strap 62 provide the primary securing function of the shoe about the foot while also stabilizing the infratalar joints.

In summary, there has been provided a stabilizing device that stabilizes motion about the infratalar joints. The stabilizing device includes a dorsal strap for disposal about the dorsum of the foot, an Achilles strap for disposal over the tendo-calcaneus adjacent the attachment point thereof to the calcaneus bone and a plantar strap for disposal under the sole of the foot exterior to the shoe and proximate the attachment point of the plantar fascia to the calcaneus bone. Each of the straps has one end thereof attached to a common connection point. The free end of the plantar strap has ring clasps attached thereto for receiving the free ends of the dorsal and Achilles straps which are inserted therethrough and then tension applied to apply force along the line of motion of the infratalar joints. The stabilizing device therefor stabilizes the infratalar joints and increases shoe-foot conformation during exercise. The adjustability on the tension on the dorsal and Achilles straps allows for adjustment during an exercise routine such that compensation is made for swelling of the foot.

Although the preferred embodiment has been described in detail, it should be understood that various changes, substitutions and alterations can be made therein, without departing from the spirit and scope of the invention as defined by the appended claims.

What is claimed is:

1. An apparatus for stabilizing movement of the infratalar joints of the foot, comprising:
   first means for applying a dispersive force about the region of the dorsum of the foot and directed along the line of motion of the infratalar joints, said first means slideable over the dorsum of the foot;
   second means for applying a dispersive force about the region of the tendo-calcaneus proximate the attachment point thereof to the calcaneus bone and directed towards the region of the posterior talo-calcanean joint;
   third means for applying a dispersive force about the sole of the foot in the region proximate the attachment point of the plantar fascia to the calcaneus bone and directed towards the infratalar joints, such that said first, second and third dispersive force means reduced movement of the infratalar joints during exercise; and
   means for adjusting the relative force and position of said first, second and third dispersive force means such that said first and second dispersive force means can have differing forces for application to the infratalar joints.

2. An apparatus for stabilizing movement of the infratalar joints of the foot, comprising:
   first means for applying a dispersive force about the region of the dorsum of the foot and directed along the line of motion of the infrataler joints;
   second means for applying a dispersive force about the region of the tendo-calcaneus proximate the attachment point thereof to the calcaneus bone and directed towards the region of the posterior talo-calcanean joint;
   third means for applying a dispersive force about the sole of the foot in the region proximate the attachment point of the plantar fascia to the calcaneus bone and directed towards the infratalar joints, such that said first, second and third dispersive force means reduced movement of the infratalar joints during exercise; and
   force relief means for reducing the magnitude of said first dispersive force means proximate to tendon insertion points on the dorsum of the foot.

3. The apparatus of claim 2 further comprising force relief means for relieving the magnitude of said second dispersive force means proximate the attachment point of said tendo-calcaneus to the calcaneal bone.

4. The apparatus of claim 1 wherein the sum of the magnitudes of said first and second dispersive force means is essentially equal to the magnitude of said third dispersive force means.

5. An apparatus for stabilizing movement of the infratalar joints of the foot, comprising;
   first means for applying a dispersive force about the region of the dorsum of the foot and directed along the line of motion of the infratalar joints;
   second means for applying a dispersive force about the region of the tendo-calcaneus proximate the attachment point thereof to the calcaneus bone and directed towards the region of the posterior talo-calcanean joint;
   third means for applying a dispersive force about the sole of the foot in the region proximate the attachment point of the plantar fascia to the calcaneus bone and directed towards the infratalar joints, such that said first, second and third dispersive force means reduced movement of the infratalar joints during exercise;
   first adjustment means for adjusting said first dispersive force means; and
   second adjustment means for adjusting said second dispersive force means, said first and second adjustment means adjusting the magnitude and angle of said first and second dispersive force means.

6. An apparatus for stabilizing movement of the infratalar joints of a foot disposed in a shoe comprising:
   a plantar strap for being disposed proximate the plantar fascia at the attachment point thereof to the calcaneus bone, said plantar strap having a first and second end for partially extending up the sides of the foot exterior to the shoe;
   a dorsal strap for being disposed on the dorsus of the foot exterior to the shoe and proximate the navicular bone, said dorsal strap having one end thereof secured to the first end of said plantar strap;
   first means for removably attaching the free end of said dorsal strap to the second end of said plantar strap;
   an Achilles strap for being disposed exterior to the shoe and adjacent the tendo-calcaneus proximate the attachment point thereof to the calcaneus bone, said Achilles strap having one end thereof secured to the first end of said plantar strap; and
   second means for removably attaching the free end of said Achilles strap to the second end of said plantar strap, said first and second attaching means enabling adjustable tensioning of said dorsal strap, said Achilles strap and said plantar strap to restrain movement of the infratalar joints during exercise.

7. The apparatus of claim 6 further comprising means for adjusting the relative tension of said dorsal strap, Achilles strap and plantar strap, the tension in said plantar strap equaling the combined tension in said dorsal strap and said Achilles strap.

8. The apparatus of claim 7 further comprising means for adjusting the lengths of said dorsal strap and said Achilles strap.

9. The apparatus of claim 6 further comprising means for relieving the force directed towards the dorsum of the foot by said dorsal strap proximate tendon insertion points.

10. The apparatus of claim 9 wherein the tendon insertion points are the points at which the tibialis anterior and the tibialis posterior tendons insert on the medial side of the foot.

11. The apparatus of claim 6 further comprising means for relieving the force applied by said Achilles straps at points adjacent the insertion point of the tendo-calcaneus.

12. The apparatus of claim 6 wherein said plantar strap, dorsal strap and Achilles strap are of a one-piece construction.

13. The apparatus of claim 6 wherein each of said first and second attaching means comprise:
   first and second loops attached to the second end of said plantar strap for receiving the free end of said dorsal strap and plantar straps, respectively;

a layer of fibrous material disposed on the ventral sides of said dorsal and Achilles straps adjacent the free end thereof; and a layer of hooklike material disposed on the exterior side of said dorsal and Achilles straps such that said layer of fibrous material mates therewith when the end of the respective one of said dorsal and Achilles straps is inserted into said loop and folded back thereover.

14. The apparatus of claim 6 wherein the first end of said plantar strap is disposed on the medial side of the foot.

15. The apparatus of claim 6 wherein the first end of said plantar strap is disposed on the lateral side of the foot.

16. The apparatus of claim 6 wherein the plantar strap is integral with the shoe.

17. An apparatus for stabilizing movement of the infratalar joints of the foot within a shoe during exercise comprising:

a plantar strap for being disposed exterior to the shoe and proximate the plantar fascia at the attachment point thereof to the calcaneus bone, said plantar strap having a medial end disposed on the medial side of the shoe and the lateral end disposed on the lateral side of the shoe;

a dorsal strap for being disposed on the shoe adjacent the dorsum of the foot proximate the navicular bone, said dorsal strap having one end thereof secured to the lateral end of said plantar strap at an angle thereto;

an Achilles strap for being disposed on the shoe adjacent the tendo-calcaneus proximate the attachment point thereof to the calcaneus bone, said Achilles strap having one end thereof secured to the medial end of said plantar strap at an angle thereto; and means for attaching the free ends of said dorsal strap and said Achilles strap to the lateral end of said plantar strap such that the lengths thereof can be selectively adjusted and the force applied to the direction of motion of the infratalar joints can be adjusted to restrain movement of the infratalar joints.

18. An apparatus for stabilizing movement of the infratalar joints of the foot within a shoe during exercise, comprising:

a first nonresilient strap for being disposed over the instep of the foot external to the shoe;

a second nonresilient strap for being disposed over the heel of the foot external to the shoe;

a third nonresilient strap for being disposed under the arch of the foot external to the shoe;

a first force relief pad disposed between said first nonresilient strap and the instep of the foot and proximate to tendon insertion points on the dorsum of the foot;

one end of said first, second and third straps connected together on the medial side of the foot in a "Y" connection; and first and second buckles disposed on the free end of said third strap proximate the lateral side of the foot for receiving the free ends of said first and second straps respectively, and allowing tensioning thereof in a "Y" connection;

said first, second and third straps stabilizing the foot along the line of motion of the infratalar joints.

* * * * *

REEXAMINATION CERTIFICATE (3569th)
United States Patent [19]
Curtis

[11] B1 4,461,288
[45] Certificate Issued Jul. 14, 1998

[54] MID-HIND FOOT STABILIZER

[75] Inventor: R. Stephen Curtis, Dallas, Tex.

[73] Assignee: Nike, Inc., Beaverton, Oreg.

Reexamination Request:
No. 90/004,573, Mar. 5, 1997

Reexamination Certificate for:
Patent No.: 4,461,288
Issued: Jul. 24, 1984
Appl. No.: 524,428
Filed: Aug. 18, 1983

[51] Int. Cl.$^6$ .................................................. A61F 5/04
[52] U.S. Cl. .................................................. 602/60; 602/62
[58] Field of Search .................................. 602/60, 62, 65, 602/66, 27

[56] References Cited

U.S. PATENT DOCUMENTS

| | | | |
|---|---|---|---|
| 459,616 | 9/1891 | Von Rohonczy . | |
| 702,476 | 6/1902 | Price . | |
| 703,828 | 7/1902 | Read . | |
| 1,155,506 | 10/1915 | Osaki . | |
| 1,283,335 | 10/1918 | Shillcock . | |
| 1,462,534 | 7/1923 | Condylis et al. . | |
| 1,944,664 | 1/1934 | Maxcy | 36/11.5 |
| 2,147,197 | 2/1939 | Glidden | 36/9 |
| 2,446,902 | 8/1948 | Brand | 128/166 |
| 2,642,677 | 6/1953 | Yates | 36/11.5 |
| 2,660,813 | 12/1953 | Shapiro | 36/2.5 |
| 2,708,930 | 5/1955 | Lowman | 128/80 |
| 2,935,798 | 5/1960 | Piberhofer | 36/2.5 |
| 3,234,667 | 2/1966 | Bovay | 36/2.5 |
| 3,327,410 | 6/1967 | Park, Sr. et al. | 36/2.5 |
| 3,464,125 | 9/1969 | Conway | 36/2.5 |
| 3,506,000 | 4/1970 | Baker | 128/166 |
| 3,699,959 | 10/1972 | Garrahan et al. | 128/166 |
| 4,200,997 | 5/1980 | Scheinhaus et al. | 36/11.5 |
| 4,236,328 | 12/1980 | Friedlander | 36/58.5 |
| 4,245,408 | 1/1981 | Larsen et al. | 36/50 |
| 4,270,285 | 6/1981 | Antonious | 36/50 |
| 4,282,657 | 8/1981 | Antonious | 36/50 |
| 4,308,672 | 1/1982 | Antonious | 36/50 |
| 4,313,433 | 2/1982 | Cramer | 128/80 H |
| 4,314,412 | 2/1982 | Anderson et al. | 36/100 |
| 4,342,161 | 8/1982 | Schmohl | 36/114 |
| 4,366,631 | 1/1983 | Larsen et al. | 36/50 |
| 4,392,487 | 7/1983 | Selner et al. | 128/80 H |
| 4,411,077 | 10/1983 | Slavitt | 36/89 |

FOREIGN PATENT DOCUMENTS

| | | |
|---|---|---|
| 31283 | 1/1908 | Austria . |
| 0047710 | 3/1982 | European Pat. Off. . |
| 0057170 | 8/1982 | European Pat. Off. . |
| 827130 | 4/1938 | France . |
| 2458241 | 1/1981 | France . |
| 31283 | 8/1884 | Germany . |
| 2402 | 1/1890 | Sweden . |
| 5832 | of 1906 | United Kingdom . |
| 10853 | of 1907 | United Kingdom . |
| 4364 | 1/1916 | United Kingdom . |

*Primary Examiner*—John D. Yasko

[57] ABSTRACT

A stabilizing strap (25) for exterior use with a shoe (28) including a dorsal strap (26), an Achilles strap (30) and a plantar strap (32). One end of the dorsal strap (26), the Achilles strap (30) and the plantar strap (32) are connected together at a point (34) on the medial side of the foot. The other end of the plantar strap (32) is attached to two connecting straps (36) and (38). Two ring clasps (42) and (44) are attached to the end of the connecting straps (36) and (38) for receiving the free ends of the dorsal strap (26) and the Achilles strap (30). A fibrous layer (52) and a hook-like layer (50) are disposed on the exterior of the Achilles strap (30) such that the free end thereof can be pulled through the ring clasp and attached thereto. A fibrous layer (48) and a hook-like layer (46) are disposed on the exterior of the dorsal strap (26) to provide a similar attachment. By tensioning the dorsal strap (26) and the Achilles strap (30), a stabilizing force can be directed along the line of motion of the infratalar joints of the foot to prevent excess pronation thereof during exercise.

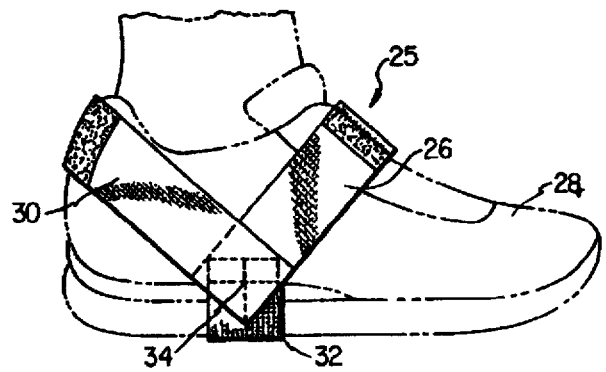

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–18 is confirmed.

\* \* \* \* \*